US011814438B2

(12) United States Patent
Monnet

(10) Patent No.: US 11,814,438 B2
(45) Date of Patent: Nov. 14, 2023

(54) FC MUTANTS WITH IMPROVED FUNCTIONAL ACTIVITY

(71) Applicant: LABORATOIRE FRANÇAIS DU FRACTIONNEMENT ET DES BIOTECHNOLOGIES, Les Ulis (FR)

(72) Inventor: Céline Monnet, Lambersart (FR)

(73) Assignee: LABORATOIRE FRANÇAIS DU FRACTIONNEMENT ET DES BIOTECHNOLOGIES, Puteaux (FR)

(*) Notice: Subject to any disclaimer, the term of this patent is extended or adjusted under 35 U.S.C. 154(b) by 336 days.

(21) Appl. No.: 16/315,356

(22) PCT Filed: Jul. 5, 2017

(86) PCT No.: PCT/EP2017/066791
§ 371 (c)(1),
(2) Date: Jan. 4, 2019

(87) PCT Pub. No.: WO2018/007453
PCT Pub. Date: Jan. 11, 2018

(65) Prior Publication Data
US 2019/0309085 A1    Oct. 10, 2019

(30) Foreign Application Priority Data

Jul. 6, 2016 (FR) ........................... 1656463

(51) Int. Cl.
C07K 16/00 (2006.01)
A61K 39/395 (2006.01)
C07K 16/28 (2006.01)
C07K 16/08 (2006.01)
C07K 16/14 (2006.01)
C07K 16/32 (2006.01)
C07K 1/00 (2006.01)

(52) U.S. Cl.
CPC .......... *C07K 16/2887* (2013.01); *C07K 16/00* (2013.01); *C07K 16/08* (2013.01); *C07K 16/14* (2013.01); *C07K 16/32* (2013.01); *C07K 2317/52* (2013.01); *C07K 2317/524* (2013.01); *C07K 2317/526* (2013.01); *C07K 2317/72* (2013.01); *C07K 2317/732* (2013.01); *C07K 2317/92* (2013.01)

(58) Field of Classification Search
None
See application file for complete search history.

(56) References Cited

U.S. PATENT DOCUMENTS

2005/0054832 A1    3/2005  Lazar et al.
2007/0003546 A1    1/2007  Lazar et al.
2012/0009188 A1*   1/2012  Behrens ............ A61P 11/06
                                                424/133.1
2014/0112926 A1*   4/2014  Liu .................. A61K 39/39558
                                                424/136.1
2016/0046722 A1*   2/2016  Chevreux ........... A61P 31/04
                                                800/6

FOREIGN PATENT DOCUMENTS

EP     2889376 A1        7/2015
WO     WO-2004/074455 A2 9/2004
WO     WO-2012/125850 A1 9/2012
WO     WO-2014/140322 A1 9/2014

OTHER PUBLICATIONS

Isoda et al. PLOS One, Oct. 7, 2015, 10(10): e0140120.doi: 1371/journal.pone.0140120, pp. 1-17. (Year: 2015).*
EP Search Report for International application No. FR 1656463 dated Apr. 24, 2017.
International Search Report and Written Opinion for International Application No. PCT/EP2017/066791 dated Jul. 5, 2017.
Oganesyan et al., "Structural characterization of a mutated, ADCC-enhanced human Fc fragment," Molecular immunology, 45(7):1872-1882 (2008).

* cited by examiner

*Primary Examiner* — Chun W Dahle
(74) *Attorney, Agent, or Firm* — NIXON & VANDERHYE

(57) ABSTRACT

The present invention relates to a variant of a parent polypeptide comprising an Fc fragment, wherein the variant exhibits an increased affinity for at least one of the Fc (FcR) fragment receptors selected from among FcγRIIIa (CD16a), FcγRIIa (CD32a), and FcγRIIb (CD32b) receptors, relative to that of the parent polypeptide, characterized in that it comprises at least one mutation chosen from among K290G, Y296W, V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, Q295I, Q295M, Y296H, S298A, S298R, Y300I, Y300V, Y300W, R301A, R301M, R301P, R301S, V302A, V302F, V302L, V302M, V302R, V302S, V303S, V303Y, S304T, V305A, V305F, V305I, V305L, V305R and V305S of the Fc fragment, wherein the numbering is that of the EU index or equivalent in Kabat.

6 Claims, 2 Drawing Sheets

Figure 2:
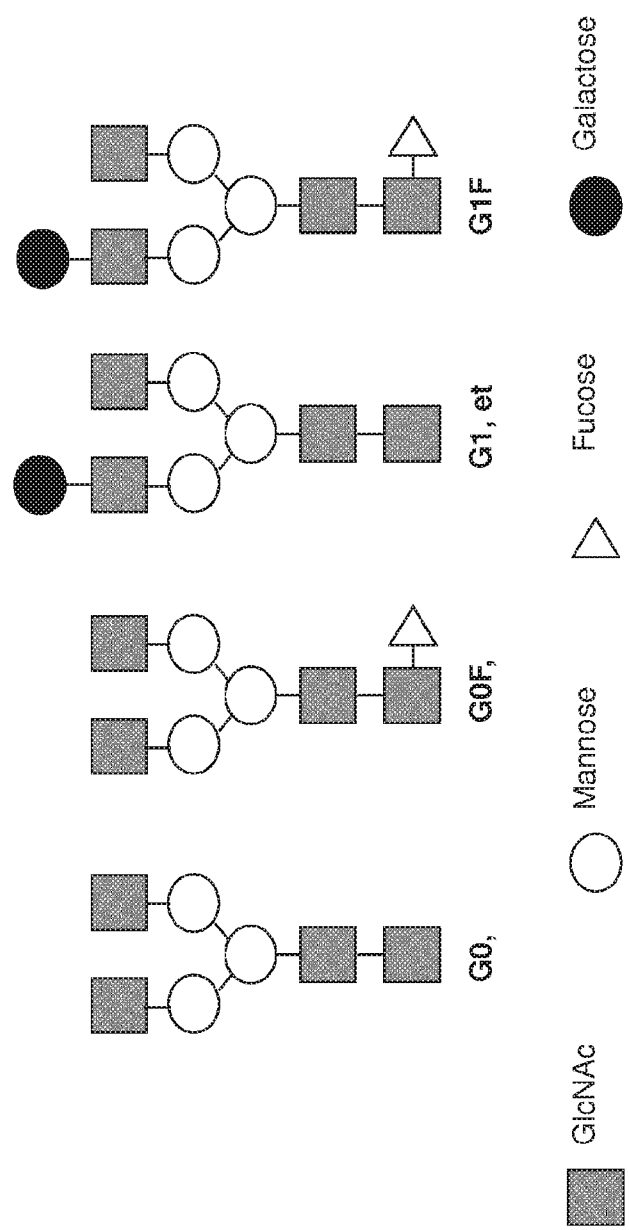

Specification includes a Sequence Listing.

|  |  |  |
|---|---|---|
| IgG1m(1,17) | EPKSCDK--THT----------------------CPPCPAPEL |  |
| IgG1m(3) | EPKSCDK--THT----------------------CPPCPAPEL |  |
| IgG2 | ERKCCVE-----------------------------CPPCPAPPV |  |
| IgG3 | ELKTPLGDTTHTCPRCPEPKSCDTPPPCPRCPEPKSCDTPPPCPRCPAPEL |  |
| IgG4 | ESKYG-------------------------------PPCPSCPAPEF |  |

226 ↑

| IgG1m(1,17) | LGGPSVFLFPPKPKDTLMISRTPEVTCVVVDVSHEDPEVKFNWYVDGVEVHNAKTKPREEQYNSTY |
| IgG1m(3) | LGGPSVFLFPPKPKDTLMISRTPEVTCVVVDVSHEDPEVKFNWYVDGVEVHNAKTKPREEQYNSTY |
| IgG2 | AGPSVFLFPPKPKDTLMISRTPEVTCVVVDVSHEDPEVQFNWYVDGVEVHNAKTKPREEQFNSTF |
| IgG3 | LGGPSVFLFPPKPKDTLMISRTPEVTCVVVDVSHEDPEVQFKWYVDGVEVHNAKTKPREEQYNSTP |
| IgG4 | LGGPSVFLFPPKPKDTLMISRTPEVTCVVVDVSQEDPEVQFNWYVDGVEVHNAKTKPREEQFNSTY |

| IgG1m(1,17) | RVVSVLTVLHQDWLNGKEYKCKVSNKALPAPIEKTISKAKGQPREPQVYTLPPSRDELTKNQVSLT |
| IgG1m(3) | RVVSVLTVLHQDWLNGKEYKCKVSNKALPAPIEKTISKAKGQPREPQVYTLPPSREEMTKNQVSLT |
| IgG2 | RVVSVLTVVHQDWLNGKEYKCKVSNKGLPAPIEKTISKTKGQPREPQVYTLPPSREEMTKNQVSLT |
| IgG3 | RVVSVLTVLHQDWLNGKEYKCKVSNKALPAPIEKTISKTKGQPREPQVYTLPPSREEMTKNQVSLT |
| IgG4 | RVVSVLTVLHQDWLNGKEYKCKVSNKGLPSSIEKTISKAKGQPREPQVYTLPPSQEEMTKNQVSLT |

| IgG1m(1,17) | CLVKGFYPSDIAVEWESNGQPENNYKTTPPVLDSDGSFFLYSKLTVDKSRWQQGNVFSCSVMHEAL |
| IgG1m(3) | CLVKGFYPSDIAVEWESNGQPENNYKTTPPVLDSDGSFFLYSKLTVDKSRWQQGNVFSCSVMHEAL |
| IgG2 | CLVKGFYPSDIAVEWESNGQPENNYKTTPPMLDSDGSFFLYSKLTVDKSRWQQGNVFSCSVMHEAL |
| IgG3 | CLVKGFYPSDIAVEWESSGQPENNYNTTPPMLDSDGSFFLYSKLTVDKSRWQQGNIFSCSVMHEAL |
| IgG4 | CLVKGFYPSDIAVEWESNGQPENNYKTTPPVLDSDGSFFLYSRLTVDKSRWQEGNVFSCSVMHEAL |

| IgG1m(1,17) | HNHYTQKSLSLSPGK | (SEQ ID NO:6) |
| IgG1m(3) | HNHYTQKSLSLSPGK | (SEQ ID NO:10) |
| IgG2 | HNHYTQKSLSLSPGK | (SEQ ID NO:7) |
| IgG3 | HNRFTQKSLSLSPGK | (SEQ ID NO:8) |
| IgG4 | HNHYTQKSLSLSLGK | (SEQ ID NO:9) |

FIG.1

SEQUENCE LISTING

<160> NUMBER OF SEQ ID NOS: 10

<210> SEQ ID NO 1
<211> LENGTH: 222
<212> TYPE: PRT
<213> ORGANISM: Artificial Sequence
<220> FEATURE:
<223> OTHER INFORMATION: Fc of IgG1 G1m1,17

<400> SEQUENCE: 1

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 2
<211> LENGTH: 221
<212> TYPE: PRT
<213> ORGANISM: Artificial Sequence
<220> FEATURE:
<223> OTHER INFORMATION: Fc of IgG2

<400> SEQUENCE: 2

```
Cys Pro Pro Cys Pro Ala Pro Pro Val Ala Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Phe Arg Val Val Ser Val Leu
65                  70                  75                  80
```

```
Thr Val Val His Gln Asp Trp Leu Asn Gly Lys Glu Tyr Lys Cys Lys
             85                  90                  95

Val Ser Asn Lys Gly Leu Pro Ala Pro Ile Glu Lys Thr Ile Ser Lys
            100                 105                 110

Thr Lys Gly Gln Pro Arg Glu Pro Gln Val Tyr Thr Leu Pro Pro Ser
            115                 120                 125

Arg Glu Glu Met Thr Lys Asn Gln Val Ser Leu Thr Cys Leu Val Lys
        130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Met Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys
        210                 215                 220

<210> SEQ ID NO 3
<211> LENGTH: 222
<212> TYPE: PRT
<213> ORGANISM: Artificial Sequence
<220> FEATURE:
<223> OTHER INFORMATION: Fc of IgG3

<400> SEQUENCE: 3

Cys Pro Arg Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
            35                  40                  45

Gln Phe Lys Trp Tyr Val Asp Gly Val Glu Val His Asn Ala Lys Thr
        50                  55                  60

Lys Pro Arg Glu Glu Gln Tyr Asn Ser Thr Phe Arg Val Val Ser Val
65                  70                  75                  80

Leu Thr Val Leu His Gln Asp Trp Leu Asn Gly Lys Glu Tyr Lys Cys
            85                  90                  95

Lys Val Ser Asn Lys Ala Leu Pro Ala Pro Ile Glu Lys Thr Ile Ser
            100                 105                 110

Lys Thr Lys Gly Gln Pro Arg Glu Pro Gln Val Tyr Thr Leu Pro Pro
            115                 120                 125

Ser Arg Glu Glu Met Thr Lys Asn Gln Val Ser Leu Thr Cys Leu Val
        130                 135                 140

Lys Gly Phe Tyr Pro Ser Asp Ile Ala Val Glu Trp Glu Ser Ser Gly
145                 150                 155                 160

Gln Pro Glu Asn Asn Tyr Asn Thr Thr Pro Pro Met Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Ile Phe Ser Cys Ser Val Met His Glu Ala Leu His
        195                 200                 205

Asn Arg Phe Thr Gln Lys Ser Leu Ser Leu Ser Pro Gly Lys
        210                 215                 220
```

<210> SEQ ID NO 4
<211> LENGTH: 222
<212> TYPE: PRT
<213> ORGANISM: Artificial Sequence
<220> FEATURE:
<223> OTHER INFORMATION: Fc of IgG4

<400> SEQUENCE: 4

```
Cys Pro Ser Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys
    210                 215                 220
```

<210> SEQ ID NO 5
<211> LENGTH: 222
<212> TYPE: PRT
<213> ORGANISM: Artificial Sequence
<220> FEATURE:
<223> OTHER INFORMATION: Fc of IgG1 G1m3

<400> SEQUENCE: 5

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95
```

```
Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 6
<211> LENGTH: 232
<212> TYPE: PRT
<213> ORGANISM: Artificial Sequence
<220> FEATURE:
<223> OTHER INFORMATION: Fc of IgG1 G1m1,17

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 7
<211> LENGTH: 228
<212> TYPE: PRT
<213> ORGANISM: Artificial Sequence
<220> FEATURE:
<223> OTHER INFORMATION: Fc of IgG2

<400> SEQUENCE: 7

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 8
<211> LENGTH: 279
<212> TYPE: PRT
<213> ORGANISM: Artificial Sequence
<220> FEATURE:
<223> OTHER INFORMATION: Fc of IgG3

<400> SEQUENCE: 8

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro Ala Pro
    50                  55                  60

Glu Leu Leu Gly Gly Pro Ser Val Phe Leu Phe Pro Pro Lys Pro Lys

```
                65                  70                  75                  80
Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
                115                 120                 125

Asn Ser Thr Phe Arg Val Val Ser Val Leu Thr Val Leu His Gln Asp
            130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
            195                 200                 205

Ile Ala Val Glu Trp Glu Ser Ser Gly Gln Pro Glu Asn Asn Tyr Asn
        210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 9
<211> LENGTH: 229
<212> TYPE: PRT
<213> ORGANISM: Artificial Sequence
<220> FEATURE:
<223> OTHER INFORMATION: Fc of IgG4

<400> SEQUENCE: 9

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
```

```
                145                 150                 155                 160
Val Glu Trp Glu Ser Asn Gly Gln Pro Glu Asn Asn Tyr Lys Thr Thr
                    165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
        210                 215                 220

Leu Ser Leu Gly Lys
225

<210> SEQ ID NO 10
<211> LENGTH: 232
<212> TYPE: PRT
<213> ORGANISM: Artificial Sequence
<220> FEATURE:
<223> OTHER INFORMATION: Fc of IgG1 G1m3

<400> SEQUENCE: 10

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
        210                 215                 220

Ser Leu Ser Leu Ser Pro Gly Lys
225                 230
```

FC MUTANTS WITH IMPROVED FUNCTIONAL ACTIVITY

CROSS-REFERENCE TO RELATED APPLICATIONS

This application is a national-stage application of International Application No. PCT/EP2017/066791, filed on Jul. 5, 2017, which claims the benefit of priority to French Application No. 16 56463, filed Jul. 6, 2016.

The present invention relates to a polypeptide comprising a mutated Fc region and having increased affinity for at least one of the Fc (FcR) fragment receptors selected from among FcγRIIIa (CD16a), FcγRIIa (CD32a), and FcγRIIb (CD32b) receptors.

Therapeutic antibodies and Fc fusion proteins are used today to treat various diseases, such as rheumatoid arthritis, psoriasis, multiple sclerosis and many forms of cancer. Therapeutic antibodies may be monoclonal or polyclonal antibodies. The monoclonal antibodies are obtained from a single antibody-producing cell line, which shows identical specificity for a single antigen.

The therapeutic effect of antibodies targeting membrane antigens includes the recruitment of effector cells expressing receptors for the crystallizable fragment of the antibodies (the "Fc receptors"). Fc receptors are proteins present on the surface of certain cells contributing to the functions of the immune system, in particular natural killer (NK) cells, macrophages, neutrophils and mast cells. There are several types, which are classified according to the type of antibodies they recognize: Fc (FcγR) gamma receptors bind to IgG, the Fc (FcαR) alpha receptor binds to IgA, and Fc (FcεR) epsilon receptors bind to IgE.

The binding of the Fc receptor with the Fc region of an antibody triggers different mechanisms as a function of the nature of the cell on which this receptor is expressed. The functional activity of the antibodies is, in particular, mediated by the binding of the Fc fragment to the Fc receptors. In view of the importance of the mechanisms linked to the binding of Fc receptors to antibodies, it would be particularly advantageous to have variants with a modified affinity, preferably increased for Fc receptors and, in particular, having a better functional activity mediated by Fc (for example, antibody-dependent cellular cytotoxicity, complement-dependent cytotoxicity, or antibody-dependent cellular phagocytosis).

The Applicant has now developed particular Fc fragments having an improved affinity for Fc receptors, in particular for at least one Fc receptor selected from among FcγRIIIa (CD16a), FcγRIIa (CD32a), FcγRIIb (CD32b), FcγRI (CD64) and the complement C1q. Advantageously, such Fc fragments have a single mutation allowing optimal control of the impact of the mutation on the binding of the Fc fragment to at least one Fc receptor and/or on its effector activities. Alternatively, such fragments may comprise at least one additional mutation, conferring advantageous properties such as increasing FcRn binding and/or increasing half-life. These fragments may be used in therapy, in order to bring greater effectiveness to the product that contains them.

CAPTIONS OF FIGURES

FIG. 1 shows alignments of native human IgG1 sequences referring to positions 216 to 447 (according to the EU index) with the corresponding sequences of human IgG2 (SEQ ID NO: 7), human IgG3 (SEQ ID NO: 8) and human IgG4 (SEQ ID NO: 9). The IgG1 sequences refer to the G1m1.17 allotype (SEQ ID NO: 6) and the G1m3 allotype (SEQ ID NO: 10). The "CH2-CH3 lower hinge" domain of IgG1 begins with cysteine 226 (see arrow). The CH2 domain is highlighted in gray while the CH3 domain is italicized.

FIG. 2 shows the forms G0, G0F, G1 and G1F of the glycan structures likely to be present on the Fc fragments of the invention.

DESCRIPTION OF THE INVENTION

The present invention relates to a variant of a parent polypeptide comprising an Fc fragment, wherein the variant has a modified affinity, preferably increased for at least one of the Fc (FcR) fragment receptors selected from among FcγRIIIa (CD16a), FcγRIIa (CD32a), and FcγRIIb (CD32b) receptors relative to that of the parent polypeptide, characterized in that it comprises at least one mutation chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, Q295I, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304T, V305A, V305F, V305I, V305L, V305R and V305S of the Fc fragment; wherein the numbering is that of the EU index or equivalent in Kabat.

Such a variant of a parent polypeptide is called "variant according to the invention" in the present application.

Throughout this application, the residue numbering in the Fc region is that of the immunoglobulin heavy chain according to the EU index or equivalent in Kabat et al. (Sequences of Proteins of Immunological Interest, 5th ed., Public Health Service, National Institutes of Health, Bethesda, Maryland, 1991). The term "EU index or equivalent in Kabat" refers to the US numbering of human IgG1, IgG2, IgG3 or IgG4 antibody residues. This is illustrated on the IMGT website (http://www.imgt.org/IMGIScientificChart/Numbering/Hu_IGHGnber.html).

FcR allow immune cells to take advantage of the specificity of the antibodies that bind to them to direct their cellular functions on the antigens and pathogens specific for that antibody.

FcγR represent the most diverse group of FcR and are the main mediators of antibody functions in the body. There are three families of human FcγR:

FcγRI (CD64);
FcγRII (CD32); and
FcγRIII (CD16).

Three of them (FcγRI, FcγRIIa, FcγRIIIa) are activating receptors, which differ in their binding affinities and in their cellular expressions.

The FcγRIIIa (CD16a) receptor is involved in antibody dependent cellular cytotoxicity (ADCC or Antibody-Dependent Cell-mediated Cytotoxicity), it has a V/F polymorphism at position 158. The FcγRIIa (CD32a) receptor is, for its part, involved in platelet activation and phagocytosis; it has an H/R polymorphism at position 131. The FcγRI (CD64) receptor is also involved in antibody-dependent cellular cytotoxicity (ADCC) and in phagocytosis mechanisms.

Finally, the FcγRIIb (CD32b) receptor is involved in the inhibition of cellular activity. Among the Fc receptors defined in the context of the invention, the C1q complement is involved in the CDC or Complement Dependent Cytotoxicity activity.

By "polypeptide" or "protein" is meant a sequence comprising at least 100 amino acids covalently attached.

By "amino acid" is meant one of the 20 naturally occurring amino acids or unnatural analogues.

The term "position" means a position in the sequence of a polypeptide. For the Fc region, the positions are numbered according to the EU index or equivalent in Kabat.

The term "antibody" is used in the common sense. It corresponds to a tetramer that includes at least one Fc region, and two variable regions. Antibodies comprise, in particular, full-length immunoglobulins, monoclonal antibodies, multi-specific antibodies, chimeric antibodies, humanized antibodies, and fully human antibodies. The amino-terminal portion of each heavy chain comprises a variable region of about 100 to 110 amino acids responsible for antigen recognition. In each variable region, three loops are pooled to form an antigen binding site. Each of the loops is called a complementarity determining region (hereinafter referred to as a "CDR"). The carboxy-terminal portion of each heavy chain defines a constant region primarily responsible for the effector function.

IgGs have several subclasses, including IgG1, IgG2, IgG3 and IgG4. IgM subclasses include IgM1 and IgM2. Thus, by "isotype" is meant one of the subclasses of immunoglobulins defined by the chemical and antigenic characteristics of their constant regions. The known isotypes of human immunoglobulins are IgG1, IgG2, IgG3, IgG4, IgA1, IgA2, IgM1, IgM2, IgD and IgE.

Full-length IgG are tetramers and consist of two identical pairs of two immunoglobulin chains, wherein each pair has a light chain and a heavy chain, and wherein each light chain comprises the VL and CL domains, and each heavy chain comprises the domains VH, Cγ1 (also called CH1), Cγ2 (also called CH2), and Cγ3 (also called CH3). In the context of a human IgG1, "CH1" refers to positions 118 to 215, "CH2" refers to positions 231 to 340, and "CH3" refers to positions 341 to 447 according to the EU index or equivalent in Kabat. The IgG heavy chain also includes an N-terminal flexible hinge domain which refers to positions 216-230 in the case of IgG1. The lower hinge range refers to positions 226 to 230 according to the EU index or equivalent in Kabat.

By "variable region" is meant the region of an immunoglobulin which comprises one or more Ig domains substantially encoded by any of the VK, VA and/or VH genes which make up the kappa, lambda and immunoglobulin heavy chains respectively. Variable regions include complementarity determining regions (CDRs) and framework regions (FRs).

The term "Fc" or "Fc region" refers to the constant region of an antibody excluding the first immunoglobulin constant region (CH1) domain. Thus Fc refers to the last two domains (CH2 and CH3) of the IgG1 constant region, and to the flexible N-terminal hinge of these domains. For a human IgG1, the Fc region corresponds to the C226 residue at its carboxy terminal end, i.e. the residues of the position 226 to 447, wherein the numbering is according to the EU index or equivalent in Kabat. The Fc region used may further comprise a portion of the upper hinge region located between positions 216 to 226 according to the EU index or equivalent in Kabat; in this case, the Fc region used corresponds to the residues of the position 216 to 447, 217 to 447, 218 to 447, 219 to 447, 220 to 447, 221 to 447, 222 to 447, 223 to 447, 224 to 447 or 225 to 447, wherein the numbering is according to the EU index or equivalent in Kabat. Preferably in this case, the Fc region used corresponds to the residues of position 216 to 447, wherein the numbering is according to the EU index or equivalent in Kabat. Preferably, the Fc region used is chosen from the sequences SEQ ID NO: 1 to 10. Preferably, the Fc fragment used is chosen from the sequences SEQ ID NO: 1, 2, 3, 4 and 5. Preferably, the Fc fragment of the parent antibody has the sequence SEQ ID NO: 1. The sequences represented in SEQ ID NO: 1, 2, 3, 4 and 5 are free of an N-terminal hinge region. The sequences represented in SEQ ID NOs: 6, 7, 8, 9 and 10 respectively correspond to the sequences represented in SEQ ID NO: 1, 2, 3, 4 and 5 with their N-terminal hinge regions. Also, in a particular embodiment, the Fc fragment of the parent antibody is chosen from the sequences SEQ ID NO: 6, 7, 8, 9 and 10. Preferably, the Fc fragment of the parent antibody has a sequence corresponding to the positions 1-232, 2-232, 3-232, 4-232, 5-232, 6-232, 7-232, 8-232, 9-232, 10-232 or 11-232 of the sequence SEQ ID NO: 6.

By "parent polypeptide" is meant a reference polypeptide. The parent polypeptide may be of natural or synthetic origin. In the context of the present invention, the parent polypeptide comprises an Fc region, referred to as the "parent Fc region". This Fc region may be selected from the group of wild type Fc regions, their fragments and mutants. Preferably, the parent polypeptide comprises a human Fc region, preferably an Fc region of a human IgG1. The parent polypeptide may include preexisting amino acid modifications in the Fc region (e.g. Fc mutant) relative to wild type Fc regions. Advantageously, the parent polypeptide is an isolated Fc region (i.e. an Fc fragment as such), a sequence derived from an isolated Fc region, an antibody, a fusion protein comprising an Fc region or an Fc conjugate, wherein this list is not limiting. By "sequence derived from an isolated Fc region" is meant a sequence comprising at least two isolated Fc regions linked together, such as an scFc (single chain Fc) or a multimer Fc. By "fusion protein comprising an Fc region" is meant a polypeptide sequence fused to an Fc region, wherein the polypeptide sequence is preferably selected from the variable regions of any antibody, the binding sequences of a receptor to its ligand, the adhesion molecules, ligands, enzymes, cytokines and chemokines. By "Fc conjugate" is meant a compound which is the result of the chemical coupling of an Fc region with a conjugation partner. The conjugation partner may be protein or non-protein. The coupling reaction generally utilizes functional groups on the Fc region and the conjugation partner. Various linking groups are known by those in the art as being suitable for the synthesis of a conjugate; for example, homo- or heterobifunctional linking groups are well known (see, Pierce Chemical Company Catalog, 2005-2006, Technical Section on Crosslinking Agents, pages 321-350). Suitable conjugation partners include therapeutic proteins, labels, cytotoxic agents such as chemotherapeutic agents, toxins and their active fragments.

Advantageously, the parent polypeptide—and therefore the variant according to the invention—consists of an Fc region.

Advantageously, the parent polypeptide—and therefore the variant according to the invention—is an antibody.

Finally, preferably, the parent polypeptide—and therefore the variant according to the invention—is a polypeptide produced in the milk of transgenic animals.

By "mutation" is meant a change of at least one amino acid of the sequence of a polypeptide, including a change of at least one amino acid of the Fc region of the parent polypeptide. The mutated polypeptide thus obtained is a variant polypeptide; it is a variant according to the invention. Such a polypeptide comprises a mutated Fc region, relative to the parent polypeptide. Preferably, the mutation is a substitution, an insertion or a deletion of at least one amino acid. By "substitution" is meant the replacement of an amino acid at a particular position in a parent polypeptide sequence by another amino acid. For example, the N434S substitution refers to a variant polypeptide, in this case a variant for which asparagine at position 434 is replaced by serine. By "amino acid insertion" or "insertion" is meant the addition of an amino acid at a particular position in a parent polypeptide sequence. For example, the insertion G>235-236 designates a glycine insertion between positions 235 and 236. By "deletion of amino acids" or "deletion" is meant the deletion of an amino acid at a particular position in a parent polypeptide sequence. For example, E294del refers to the deletion of glutamic acid at position 294. Preferably, the following mutation label is used: "434S" or "N434S", and means that the parent polypeptide comprises asparagine at position 434, which is replaced by serine in the variant. In the case of a combination of substitutions, the preferred format is "259I/315D/434Y" or "V259I/N315D/N434Y". This means that there are three substitutions in the variant, at positions 259, 315 and 434, and that the amino acid at position 259 of the parent polypeptide, namely valine, is replaced by isoleucine, that the amino acid at position 315 of the parent polypeptide, asparagine, is replaced by aspartic acid and the amino acid at position 434 of the parent polypeptide, asparagine, is replaced by tyrosine.

The variant according to the invention has a functional activity mediated by the modified Fc region, preferably increased relative to that of the parent polypeptide. By "functional activity mediated by the Fc region" is meant, in particular, the effector functions. Functional activity mediated by the Fc region thus includes, in particular, antibody-dependent cellular cytotoxicity (ADCC), complement-dependent cytotoxicity (CDC) or antibody-dependent cellular phagocytosis (ADCP), endocytosis activity, cytokine secretion, or a combination of at least two of these activities. Preferably, the functional activity mediated by the Fc region considered in the invention is selected from ADCC, ADCP, CDC and their combination. This functional activity may be evaluated by methods well known to those skilled in the art. The functional activity mediated by the Fc region of the variant according to the invention is increased relative to that of the parent polypeptide, typically by a ratio at least equal to 2, preferably greater than 5, preferably greater than 10, preferably greater than 15, preferably greater than 20, preferably greater than 25, and preferably greater than 30. Preferably, the mutated Fc region has a modified affinity, preferably increased, for at least one of the FcR. Preferably, the affinity is increased, relative to that of the parent Fc, by a ratio of at least 2, preferably greater than 5, preferably greater than 10, preferably greater than 15, preferably greater than 20, preferably greater than 25, and preferably greater than 30. In other words, the affinity of the mutated Fc region for a FcR is greater than that of the parent polypeptide.

The affinity of a polypeptide comprising an Fc region for an FcR may be evaluated by methods well known to those skilled in the art. For example, those skilled in the art can determine affinity (Kd) using surface plasmon resonance (SPR). Alternatively, those skilled in the art may perform an appropriate ELISA test. An appropriate ELISA assay compares the binding forces of the parent Fc and the mutated Fc. The detected signals specific to the mutated Fc and the parent Fc are compared. Binding affinity may be determined either by evaluating whole polypeptides or evaluating isolated Fc regions thereof.

Preferably, the mutated Fc region of the variant according to the invention comprises from 1 to 20 mutations relative to the parent polypeptide, preferably from 2 to 20 mutations. By "from 1 to 20 amino acid changes" is meant 1, 2, 3, 4, 5, 6, 7, 8, 9, 10, 11, 12, 13, 14, 15, 16, 17, 18, 19 and 20 amino acid mutations. Preferably, it comprises from 1 to 15 mutations, preferably from 2 to 15 mutations, preferably from 1 to 10 mutations relative to the parent polypeptide, preferably from 2 to 10 mutations.

Preferably, the variant according to the invention is characterized in that the mutation is chosen from an insertion, a substitution, preferably one-off, and a deletion.

Preferably, the variant according to the invention comprises at least one mutation i) chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, Q295I, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304I, V305A, V305F, V305I, V305L, V305R and V305S of the Fc fragment; wherein the numbering is that of the EU index or equivalent in Kabat.

In a particular embodiment, the invention relates to a variant of a parent polypeptide comprising an Fc fragment, wherein the variant has a modified affinity, preferably increased for at least one of the Fc (FcR) fragment receptors selected from among the FcγRIIIa (CD16a), FcγRIIa (CD32a) and FcγRIIb (CD32b) receptors relative to that of the parent polypeptide, characterized in that it comprises a single mutation i) chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, 02951, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304I, V305A, V305F, V305I, V305L, V305R and V305S of the Fc fragment; wherein the numbering is that of the EU index or equivalent in Kabat.

Thus, in a particular embodiment, the variant according to the invention comprises a single mutation i) chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, 02951, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304T, V305A, V305F, V305I, V305L, V305R and V305S of the Fc fragment; wherein the numbering is that of the EU index or equivalent in Kabat.

In another particular embodiment, the variant Fc comprises at least two mutations i), wherein the mutations are chosen from among i) V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, 02951, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304T, V305A, V305F, V305I, V305L, V305R and V305S of the Fc fragment; wherein the numbering is that of the EU index or equivalent in Kabat and with the condition that the mutations are not identical.

In a more particular embodiment, the variant Fc comprises at least three mutations i), wherein the mutations i) are chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294A, E294R, E294T, E294V, 02951, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304I, V305A, V305F, V305I, V305L, V305R and V305S of the Fc fragment; wherein the numbering is that of the EU index or equivalent in Kabat and with the condition that the mutations are not identical.

In a more particular embodiment, the variant Fc comprises at least four mutations i), wherein the mutations i) are chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294A, E294R, E294T, E294V, 02951, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304I, V305A, V305F, V305I, V305L, V305R and V305S of the Fc fragment; wherein the numbering is that of the EU index or equivalent in Kabat and with the condition that the mutations are not identical.

In one embodiment, the variant according to the invention has an increased affinity for the FcγRIIIa (CD16a) receptor. In this particular embodiment, the variant comprises at least one mutation i) chosen from among S298A, S298R, F243S, F243L, L242A, L242F, L242G, L242I, L242K, L242S, L242V, V240I, V240M, V240N, V240S, E258I, T260A, K290D, K290E, K290G, K290H, K290Q, K290S, K290Y, Y296H, Y296W of the Fc fragment; wherein the numbering is that of the EU index or equivalent in Kabat.

In another embodiment, the variant according to the invention has an increased affinity for the FcγRIIa (CD32a) receptor. In this particular embodiment, the variant comprises at least one mutation i) chosen from among F241H, F241Y, F243L, L242A, L242F, L242G, L242H, L242I, L242K, L242P, L242S, L242T, L242V, V240H, V240I, V240M, V240S, E258G, E258I, E258R, E258M, E258Q, E258Y, S267A, S267Q, S267V, T260A, T260H, T260I, T260M, T260N, T260R, T260S, T260W, V259C, V259I, V259L, V262A, V262S, V263T, V264L, V264S, V264T, V266L, V266M, E293A, E293D, E293G, E293M, E293Q, E293S, E293T, E294A, E294G, E294P, E294Q, E294R, E294T, E294V, K290D, K290E, K290G, K290H, K290L, K290N, K290Q, K290R, K290S, K290Y, P291G, P291Q, P291R, Q295I, Q295M, R292I, R292L, R301A, R301P, R301S, S304I, V302A, V302F, V302L, V302M, V302R, V302S, V303Y, V305A, V305F, V305L, V305R, V305S, Y300I, Y300V or Y300W; wherein the numbering is that of the EU index or equivalent in Kabat.

In another embodiment, the variant according to the invention has an increased affinity for the FcγRIIb (CD32b) receptor. In this particular embodiment, the variant comprises at least one mutation i) chosen from among E258R, E258Y, V262A, S267A, S267Q, S267V, V264S, V266L, V266M, K290R, R301A, R301M, S304I, V302A, V302L, V302R, V303S, V305A, V305F, V305I, V305R, Y300V of the Fc fragment; wherein the numbering is that of the EU index or equivalent in Kabat.

Preferably, the variant according to the invention is characterized in that the Fc fragment of the parent polypeptide already comprises at least:
(ii) a mutation selected from 378V, 378T, 434Y and 434S; and
(iii) at least one mutation selected from 226G, P228L, P228R, 230S, 230T, 230L, 241L, 264E, 307P, 315D, 330V, 362R, 378V, 378T, 389T, 389K, 434Y and 434S, wherein the numbering is that of the EU index or equivalent in Kabat and with the condition that mutations (ii) and (iii) do not occur on the same amino acids.

Thus according to a particular aspect, the invention relates to a variant of a parent polypeptide comprising an Fc fragment, wherein the variant has a modified affinity, preferably increased, for at least one of the Fc (FcR) fragment receptors chosen from among the FcγRIIIa (CD16a), FcγRIIa (CD32a), and FcγRIIb (CD32b) receptors relative to that of the parent polypeptide, characterized in that it comprises at least one mutation i) chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, Q295I, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304I, V305A, V305F, V305I, V305L, V305R and V305S of the Fc fragment; and further comprising at least:
  (ii) a mutation selected from among 378V, 378T, 434Y and 434S; and
  (iii) at least one mutation selected from among 226G, P228L, P228R, 230S, 230T, 230L, 241L, 264E, 307P, 315D, 330V, 362R, 378V, 378T, 389T, 389K, 434Y and 434S, with the condition that the mutations (ii) and (iii) do not occur on the same amino acids, wherein the numbering is that of the EU index or equivalent in Kabat.

In a particular embodiment, the variant comprises at least one combination of mutations selected from the group consisting of 226G/315D/434Y, 230S/315D/434Y, 230T/315D/434Y, 230T/264E/434S, 230T/389T/434S, 241 L/264E/378V, 241 L/264E/434S, 250A/389K/434Y, 259I/315D/434Y, 264E/378T/396L, 264E/378V/416K, 264E/378V/434S, 264E/396L/434S, 294del/307P/434Y, 307P/378V/434Y, 315D/330V/434Y, 315D/382V/434Y and 378V/383N/434Y, wherein it should be understood that the numbering of the amino acid positions of the Fc fragment is that of the EU index or equivalent in Kabat.

In a particular embodiment, the variant further comprises at least one mutation selected from among the group consisting of 226G, 227L, 230S, 230T, 230L, 231T, 241L, 243L, 250A, 256N, 259I, 264E, 265G, 267R, 290E, 294del, 303A, 305A, 307P, 307A, 308I, 315D, 322R, 325S, 327V, 330V, 342R, 347R, 352S, 361D, 362R, 362E, 370R, 378V, 378T, 382V, 383N, 386R, 386K, 387T, 389T, 389K, 392R, 395A, 396L, 397M, 403T, 404L, 415N, 416K, 421T, 426T, 428L, 433R, 434Y, 434S and 439R, wherein it should be understood that the numbering of the amino acid positions of the Fc fragment is that of the EU index or equivalent in Kabat.

In a particular embodiment, the variant comprises at least one combination of mutations selected from the group consisting of 307A/315D/330V/382V/389T/434Y, 256N/378V/383N/434Y, 315D/330V/361D/378V/434Y, 259I/315D/434Y, 230S/315D/428L/434Y, 241L/264E/307P/378V/433R, 250A/389K/434Y, 305A/315D/330V/395A/434Y, 264E/386R/396L/434S/439R, 315D/330V/362R/434Y, 294del/307P/434Y, 305A/315D/330V/389K/434Y, 315D/327V/330V/397M/434Y, 230I/241L/264E/265G/378V/421I, 264E/396L/415N/434S, 227L/264E/378V/434S, 264E/378T/396L, 230T/315D/362R/426T/434Y, 226G/315D/330V/434Y, 230L/241L/243L/264E/307P/378V, 250A/315D/325S/330V/434Y, 290E/315D/342R/382V/434Y, 241L/315D/330V/392R/434Y, 241 L/264E/307P/378V/434S, 230T/264E/403T/434S, 264E/378V/416K, 230T/315D/362E/434Y, 226G/315D/434Y, 226G/315D/362R/434Y, 226G/264E/347R/370R/378V/434S, 308I/315D/330V/382V/434Y, 230T/264E/378V/434S, 231I/241 L/264E/378T/397M/434S, 230 L/264E/378V/434S, 230I/315D/330V/386K/434Y, 226G/315D/330V/389T/434Y, 267R/307P/378V/421T/434Y, 230S/315D/387T/434Y, 230S/264E/352S/378V/434S and 230T/303A/322R/389T/404L/434S, wherein it should be understood that the numbering of the amino acid positions of the Fc fragment is that of the EU index or equivalent in Kabat.

In a particular embodiment, the variant according to the invention comprises at least one mutation i), preferably a single mutation i), chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, I260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, O2951, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304I, V305A, V305F, V305I, V305L, V305R and V305S of the Fc fragment; and a combination of mutations ii) and iii) selected from among 315D/330V/361D/378V/434Y, 230S/315D/428L/434Y, 307A/315D/330V/382V/389T/434Y, 259I/315D/434Y, 256N/378V/383N/434Y.

Preferably, the variant according to the invention is characterized in that the Fc fragment of the parent polypeptide already comprises at least:
  (iv) a mutation selected from 307N, 326E, 326T, 334N, 334R, 352L, 378V, 378T, 394P, 396L, 397M, 421T; and
  (v) at least one mutation selected from among 226Y, 227S, 230S, 231V, 234P, 2431, 243L, 246R, 246E, 247T, 248E, 253F, 254F, 255W, 259A, 261R, 262A, 263A, 266M, 267N, 267G, 274E, 274R, 276S, 278H, 282A, 283G, 284L, 2861, 286Y, 287T, 288E, 288R, 290E, 298N, 302A, 305A, 307P, 308A, 308I, 308G, 309P, 312G, 315D, 316D, 319H, 320T, 320R, 320M, 322E, 3231, 325S, 333G, 334N, 334R, 336T, 339T, 340E, 343S, 345G, 349S, 349H, 350A 352S, 359A, 361H, 362R, 3631, 366A, 373D, 375R, 377T, 378V, 378T, 379A, 380G, 383R, 385R, 389S, 389T, 392R, 393A, 393I, 394P, 396L, 397I, 397M, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N, wherein the numbering is that of the EU index or equivalent in Kabat and with the condition that mutations (iv) and (v) do not occur on the same amino acids.

Thus according to a particular aspect, the invention relates to a variant of a parent polypeptide comprising an Fc fragment, wherein the variant has a modified affinity, preferably increased, for at least one of the Fc (FcR) fragment receptors chosen from among the FcγRIIIa (CD16a), FcγRIIa (CD32a), and FcγRIIb (CD32b) receptors relative to that of the parent polypeptide, characterized in that it comprises at least one mutation i) chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, Q295I, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304T, V305A, V305F, V305I, V305L, V305R and V305S of the Fc fragment; and further comprising at least:

(iv) a mutation selected from among 307N, 326E, 326T, 334N, 334R, 352L, 378V, 378T, 394P, 396L, 397M, 421T; and (v) at least one mutation selected from among 226Y, 227S, 230S, 231V, 234P, 243I, 243L, 246R, 246E, 247T, 248E, 253F, 254F, 255W, 259A, 261R, 262A, 263A, 266M, 267N, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 315D, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378V, 378T, 379A, 380G, 383R, 385R, 389S, 389T, 392R, 393A, 393I, 394P, 396L, 397I, 397M, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N, wherein the numbering is that of the EU index or equivalent in Kabat and with the proviso that mutations (i), (iv) and (v) do not occur on the same amino acids.

Preferably, the mutation (iv) is selected from among 378V, 396L and 397M. Preferably, the polypeptide further comprises a mutation selected from among 248E, 326T, 333G and 423Y.

Preferably, the mutation (v) according to the invention is chosen from among 226Y, 227S, 230S, 231V, 234P, 243I, 243L, 246R, 246E, 247T, 248E, 253F, 254F, 255W, 259A, 261R, 262A, 263A, 266M, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378T, 379A, 380G, 383R, 385R, 389S, 389T, 392R, 393A, 393I, 394P, 396L, 397I, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N.

In one embodiment, the mutation (iv) is selected from 378V, 396L and 397M and the mutation (v) is selected from 248E, 316D, 326E, 333G, 378T, 396L and 421T.

In another embodiment, mutation (iv) is 378V and mutation (v) is selected from among 298N and 336T.

In another embodiment, the mutation (iv) is selected from among 378V, 396L and 397M; and mutation (v) is selected from among 231V, 286I, 286Y, 290E, 315D, 334N, 352S, 361H, 366A, 378T, 397M, 412M, 421T and 423Y.

In another embodiment, the mutation (iv) is 378V; and mutation (v) is selected from among 248E, 308A, 334R, 447N.

In another embodiment, the mutation (iv) is selected from among 378V, 326E, 397M, 334N and 396L; and mutation (v) is selected from among 316D, 397M, 334N, 248E, 231V, 246R, 336T, 421T, 361H, 366A, 439R, 290E, 394P, 307P, 378V, 378T, 286I, 286Y and 298N.

In another embodiment, the mutation (iv) is selected from among 378V, 326E, 397M, 307N, 394P, 326T, 396L and 334N; and mutation (v) is selected from among 316D, 334R, 334N, 323I, 231V, 246R, 336T, 378T, 286Y, 286I, 352S, 383R, 359A, 421T, 361H, 315D, 366A, 290E, 307P and 439R. Preferably, mutation (v) is selected from among 316D, 334R, 334N, 323I, 231V, 246R, 336T, 378T, 286Y, 286I, 352S, 383R, 359A, 421T, 361H, 366A, 290E, 307P and 439R.

In another embodiment, the mutation (iv) is selected from among 326E, 326T, 378V, 397M, 352L, 394P, 396L and 421T; and mutation (v) is selected from among 316D, 334R, 248E, 334N, 418P, 231V, 320E, 402D, 359A, 383R, 421T and 361H.

In another embodiment, the mutation (iv) is selected from among 378V, 378T, 396L, 421T, 334R and 326E; and mutation (v) is selected from among 361H, 290E, 316D, 248E, 410R, 421T, 334R, 394P, 307P, 447N, 378V, 284L, 421T, 396L, 286I, 315D and 397M.

In another embodiment, the mutation (iv) is selected from among 378V, 326E, 397M, 334N and 396L; and mutation (v) is selected from among 316D, 397M, 334N, 248E, 231V, 246R, 336T, 421T, 361H, 366A, 439R, 290E, 394P, 307P, 378V, 378T, 286I, 286Y and 298N.

In another embodiment, the mutation (iv) is selected from among 326E, 326T, 352L, 378V, 378T, 396L, 397M, 421T, 334N, 334R, 307N and 394P, and mutation (v) consists of at least 2 mutations selected from among 226Y, 227S, 230S, 231V, 234P, 243I, 243L, 246R, 246E, 247T, 248E, 253F, 254F, 255W, 259A, 261R, 262A, 263A, 266M, 267N, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 315D, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378V, 378T, 379A, 380G, 383R, 385R, 389S, 389T, 392R, 393A, 393I, 394P, 396L, 397I, 397M, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N.

Preferably, the at least 2 mutations (v) are selected from among 226Y, 227S, 230S, 231V, 234P, 243I, 243L, 246R, 246E, 247T, 248E, 253F, 254F, 255W, 259A, 261R, 262A, 263A, 266M, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378T, 379A, 380G, 383R, 385R, 389S, 389T, 392R, 393A, 393I, 394P, 396L, 397I, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P, and 447N.

Preferably, the mutated Fc region of the polypeptide according to the invention comprises a combination of mutations chosen from among the combinations:
K320E/T394P/G402D;
K290E/K320E/T350A/P396L;
T359A/S383R/V397M.

According to another aspect of the invention, there is used a composition comprising a plurality of variants of a parent polypeptide comprising an Fc fragment, all of which have substantially the same sequence, wherein the variants comprise Fc fragments which, taken as a whole, exhibit a particular glycosylation profile.

According to one particular aspect, the Fc fragments of the variants within a composition used in the context of the invention, have N-glycans on their glycosylation site (Asn 297, wherein the numbering is that of the EU index or equivalent in Kabat), characterized in that the N-glycans of the Fc fragments have a degree of fucosylation of less than 65%, preferably less than 60%, preferably less than 55%, preferably less than 50%, preferably less than 45%, preferably less than 40%, preferably less than 35%, preferably less than 30%, preferably less than 25%, preferably less than 20%.

According to another aspect, the Fc fragments of the variants within a composition used in the context of the invention have N-glycans on their glycosylation site (Asn 297), characterized in that the N-glycans of the fragments Fc have a glycan structure of biantennary type, with short chains, a weak sialylation, presenting non-intermediate terminal N-acetylglucosamines.

According to a more particular aspect, the Fc fragments of the variants within a composition used in the context of the invention have N-glycans on their glycosylation site (Asn 297), characterized in that the N-glycans of the Fc fragments have a content greater than 60% for the forms G0+G1+G0F+G1F, wherein the G0F+G1F forms are less than 50%.

According to another more particular aspect, the Fc fragments of the variants within a composition used in the context of the invention have N-glycans at their glycosylation site (Asn 297), characterized in that the N-glycans of Fc fragments have a content greater than 60% for the forms G0+G1+G0F+G1F, wherein the fucose content is less than 65%. According to another even more particular aspect, the Fc fragments of the variants within a composition used in the context of the invention have N-glycans on their glycosylation site (Asn 297), characterized in that the N-glycans of the Fc fragments have a content of less than 40% for G1F+G0F forms.

According to a more particular aspect, the Fc fragments of the variants within a composition used in the context of the invention have N-glycans at their glycosylation site (Asn 297), wherein the N-glycans of the Fc fragments have a fucosylation equal to 0%. The invention thus provides a composition comprising variants of a parent polypeptide comprising an Fc fragment, wherein the Fc fragments of the variants have N-glycans on the Asn297 glycosylation site characterized in that said N-glycans of the Fc fragments are devoid of fucose.

Also, according to one particular aspect, the Fc fragments of the variants within a composition used in the context of the invention have N-glycans on the Asn297 glycosylation site, characterized in that the N-glycans of the Fc fragments present a fucosylation rate of between 20% and 55%. In particular, the invention provides a composition comprising variants of a parent polypeptide comprising an Fc fragment, wherein the Fc fragments of the variants have N-glycans on the Asn297 glycosylation site characterized in that the N-glycans of the Fc fragments present a fucosylation rate of between 20% and 50%, between 25% and 55%, between 25% and 50%, between 20% and 45% or between 25% and 45%.

According to a more particular aspect, a composition that is useful according to the invention comprises variants of a parent polypeptide comprising an Fc fragment, wherein the Fc fragments of the variants have N-glycans on the Asn297 glycosylation site, characterized in that Fc fragments have a content greater than 60%, preferably greater than 80%, for the forms G0+G1+G0F+G1F, while the forms G0F+G1F have less than 50%, preferably less than 40%, or 30%.

According to another more particular aspect, the N-glycans of the Fc fragments within the composition have a content greater than 60% for the forms G0+G1+G0F+G1F, wherein the fucose content is less than 65%.

According to yet another more particular aspect, the N-glycans of the Fc fragments within the composition have a content of less than 50% for the G1F+G0F forms, preferably less than 40%, or 30%.

The G0, G0F, G1 and G1F forms are selected from the forms shown in FIG. 2.

Advantageously, the N-glycans of the Fc fragments within the variant composition have an average sialic acid content of less than 25%, 20%, 15%, or 10%, preferably 5%, 4% or 3%. 2%.

A composition which may be used in the context of the invention comprises variants of a parent polypeptide comprising an Fc fragment, wherein the Fc fragments of the variants have N-glycans on their glycosylation site (Asn 297), wherein the N-glycans of the Fc fragments have a glycan structure of biantennary type, with short chains, weak sialylation, and low fucosylation, while the N-glycans have, for example, a content greater than 60% for the G0+G1+G0F+G1F forms, and fucosylation of less than 60%, preferably less than 55%, while the N-glycans have, for example, a content of less than 50% of the G0F+G1F forms and a fucosylation of less than 55%.

In a particular embodiment, the Fc fragments according to the invention have glycanic structures as described in the patent application WO01/77181.

According to an advantageous embodiment, the Fc fragments used in the invention comprise at least one mutation of an amino acid with respect to a parent Fc fragment, and have N-glycans on their glycosylation site (Asn 297), wherein the N-glycans of the Fc fragments have a degree of fucosylation of less than 65%, preferably less than 60%, preferably less than 55%, preferably less than 50%, preferably less than 45%, preferably less than 40% preferably less than 35%, preferably less than 30%, preferably less than 25%, preferably less than 20%. Preferably, the Fc fragments carry at least one mutation i) chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293A, E293S, E293T, E294A, E294G, E294P, E294Q, E294R, E294T, E294V, Q295I, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304I, V305A, V305F, V305I, V305L, V305R and V305S of the Fc fragment; wherein the numbering is that of the EU index or equivalent in Kabat, and furthermore have N-glycans on their glycosylation site (Asn 297), wherein the N-glycans have a fucosylation level of less than 55%, preferably less than 50%, of preferably less than 45%, preferably less than 40%, preferably less than 35%, preferably less than 30%, preferably less than 25%, preferably less than 20%.

More preferably, the Fc fragments of the composition according to the invention carry a mutation i) chosen from among V240H, F241H, F241Y, L242H, L242P, L242T, E258G, E258R, E258M, E258Q, E258Y, V259C, V259I, V259L, T260H, T260I, T260M, T260N, T260R, T260S, T260W, V262A, V262S, V263T, V264L, V264S, V264T, V266L, V266M, S267A, S267Q, S267V, K290L, K290N, K290R, P291G, P291Q, P291R, R292I, R292L, E293A, E293D, E293G, E293M, E293Q, E293S, E293T, E294A, E294G, E294P, E294Q, E294R, E294T, E294V, 02951, Q295M, Y300I, Y300V, Y300W, R301A, R301M, R301P, R301S, V302A, V302F, V302L, V302M, V302R, V302S, V303S, V303Y, S304I, V305A, V305F, V305I, V305L, V305R and V305S, of the Fc fragment; wherein the numbering is that of the EU index or equivalent in Kabat, and furthermore have N-glycans on their glycosylation site (Asn 297), wherein the N-glycans have a fucosylation level of less than 55%, preferably less than 50%, preferably less than 45%, preferably less than 40%, preferably less than 35%, preferably less than 30%, preferably less than 25%, preferably less than 20%.

Advantageously, the Fc fragments having a modified glycosylation at the site of glycosylation at position 297, in particular a low fucosylation, show an increase in the binding of the fragment to Fc gamma (FcγR) receptors, in particular the FcγRIIIa (CD16a) receptor.

Preferably, the Fc fragments have an affinity for CD16a of at least $2 \times 10^6$ M$^{-1}$, at least equal to $2 \times 10^7$ M$^{-1}$, $2 \times 10^8$ M$^{-1}$ or $2 \times 10^9$ M$^{-1}$, as determined by Scatchard analysis or BIAcore technology (label-free surface plasmon resonance based technology).

Preferably, the variant according to the invention is characterized in that it comprises from 1 to 20 mutations of the Fc fragment, preferably from 1 to 10 mutations.

Preferably, the variant according to the invention is characterized in that the parent polypeptide comprises a parent Fc fragment, which is a human Fc fragment, preferably an Fc fragment of a human IgG1 or a human IgG2.

Preferably, the variant according to the invention is characterized in that it is chosen from an isolated Fc fragment, a sequence derived from an isolated Fc fragment, an antibody and a fusion protein comprising an Fc fragment.

Preferably, the variant according to the invention is characterized in that it is an antibody.

The present invention also relates to a polypeptide composition according to the invention.

The present invention also relates to a pharmaceutical composition comprising (1) a variant according to the invention or a composition as described in the preceding paragraph, and (2) at least one pharmaceutically acceptable excipient.

The object of the present invention is also the variant according to the invention or the composition as described above, for its use as a medicament.

As indicated previously, advantageously, the parent polypeptide—and therefore the variant according to the invention—is an antibody. In this case, the antibody may be directed against an antigen selected from a tumor antigen, a viral antigen, a bacterial antigen, a fungal antigen, a toxin, a membrane or circulating cytokine and a membrane receptor.

When the antibody is directed against a tumor antigen, its use is particularly suitable in the treatment of cancers. By "cancer" is meant any physiological condition characterized by an abnormal proliferation of cells. Examples of cancers include carcinomas, lymphomas, blastomas, sarcomas (including liposarcomas), neuroendocrine tumors, mesotheliomas, meningiomas, adenocarcinomas, melanomas, leukemias and lymphoid malignancies, wherein this list is not exhaustive.

When the antibody is directed against a viral antigen, its use is particularly suitable for the treatment of viral infections. Viral infections include infections caused by HIV, a retrovirus, a Coxsackie virus, smallpox virus, influenza, yellow fever, West Nile, a cytomegalovirus, rotavirus or Hepatitis B or C, wherein this list is not exhaustive.

When the antibody is directed against a toxin, its use is particularly suitable for the treatment of bacterial infections, for example infections with tetanus toxin, diphtheria toxin, anthrax toxins *Bacillus anthracis*, or in the treatment of infections by botulinum toxins, ricin toxins, shigatoxins, wherein this list is not exhaustive.

When the antibody is directed against a cytokine, its use is particularly useful in the treatment of inflammatory and/or autoimmune diseases. Inflammatory and/or autoimmune diseases include thrombotic thrombocytopenic purpura (ITP), transplant or organ rejection, graft-versus-host disease, rheumatoid arthritis, systemic lupus erythematosus, various types of sclerosis, primary Sjögren's syndrome (or Sjögren's syndrome), autoimmune polyneuropathies such as multiple sclerosis, type I diabetes, autoimmune hepatitis, ankylosing spondylitis, Reiter's syndrome, gout arthritis, celiac disease, Crohn's disease, chronic Hashimoto's thyroiditis (hypothyroidism), Adisson's disease, autoimmune hepatitis, Graves' disease (hyperthyroidism), ulcerative colitis, vasculitis like systemic vasculitis associated with ANCAs (anti-cytoplasmic antibodies to neutrophils), autoimmune cytopenia and other haematological complications in adults and children, such as acute or chronic autoimmune thrombocytopenia, autoimmune haemolytic anemias, haemolytic disease of the newborn (MHN), cold agglutinin disease, autoimmune acquired haemophilia; Goodpasture syndrome, extra-membranous nephropathies, autoimmune bullous skin disorders, refractory myasthenia gravis, mixed cryoglobulinemia, psoriasis, juvenile chronic arthritis, inflammatory myositis, dermatomyositis and systemic autoimmune disorders of the child including antiphospholipid syndrome, connective tissue disease, pulmonary autoimmune inflammation, Guillain-Barré syndrome, chronic inflammatory demyelinating polyradiculoneuropathy (PDCI), autoimmune thyroiditis, diabetes mellitus, myasthenia gravis, inflammatory autoimmune disease of the eye, optic neuromyelitis (Devic's disease), scleroderma, pemphigus, insulin resistance diabetes, polymyositis, Biermer's anemia, glomerulonephritis, Wegener's disease, Horton's disease, periarthritis nodosa and Churg and Strauss syndrome, Still's disease, polychondritis trophic, Behçet's disease, monoclonal gammopathy, Wegener's granulomatosis, lupus, ulcerative colitis, psoriatic arthritis, sarcoidosis, collagenous colitis, dermatitis herpetiformis, familial Mediterranean fever, IgA-deposition glomerulonephritis Lambert-Eaton myasthenic syndrome, sympathetic ophthalmia, Fiessinger-Leroy-Reiter syndrome and uveo-meningoencephalic syndrome.

Other inflammatory diseases are also concerned, such as acute respiratory distress syndrome (ARDS), acute septic arthritis, adjuvant arthritis, allergic encephalomyelitis, allergic rhinitis, allergic vasculitis, allergy, asthma, atherosclerosis, chronic inflammation due to chronic bacterial or viral infections, chronic obstructive pulmonary disease (COPD), coronary heart disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiorgan organ dysfunction syndrome (MODS), pulmonary fibrosis, sepsis and septic shock, Stevens-Johnson syndrome, undifferentiated arthritis, and undifferentiated spondyloarthropathies.

In a particular embodiment of the invention, the autoimmune disease is idiopathic thrombotic purpura (ITP) and chronic inflammatory demyelinating polyradiculoneuropathy (PDCI).

The object of the present invention is also a method for producing a variant of a parent polypeptide comprising an Fc fragment, wherein the variant has an increased affinity for at least one of the Fc (FcR) fragment receptors selected from among FcγRIIIa (CD16a), FcγRIIa (CD32a), and FcγRIIb (CD32b) receptors relative to that of the parent polypeptide, which comprises a step of mutating at least one amino acid, the mutation being chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293A, E293S, E293T, E294A, E294G, E294P, E294Q, E294R, E294T, E294V, Q295I, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304T, V305A, V305F, V305I, V305L, V305R and V305S, of the Fc fragment; wherein the numbering is that of the EU index or equivalent in Kabat.

The object of the present invention is, in particular, a method for producing a variant of a polypeptide comprising an Fc fragment, wherein the variant has an increased affinity for at least one of the Fc (FcR) fragment receptors selected from among FcγRIIIa (CD16a), FcγRIIa (CD32a), and FcγRIIb (CD32b) receptors, relative to that of the parent polypeptide, a ratio at least equal to 2, preferably greater than 5, preferably greater than 10, preferably greater than 15, preferably greater than 20, preferably greater than 25, preferably greater than 30, and which comprises a step of mutating at least one amino acid, wherein the mutation is chosen from among V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293A, E293S, E293T, E294A, E294G, E294P, E294Q, E294R, E294T, E294V, 02951, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304T, V305A, V305F, V305I, V305L, V305R and V305S, of the Fc fragment; wherein the numbering is that of the EU index or equivalent in Kabat.

The sequences described in this application may be summarized as follows:

| SEQ ID NO: | Protein | Sequence |
|---|---|---|
| 1 | Fc region of human IgG1 G1m1.17 (residues 226-447 according to the EU index or equivalent in Kabat) without an N-terminal upper hinge region | CPPCPAPELLGGPSVFLFPPKPKDTLMISRTP EVTCVVVDVSHEDPEVKFNWYVDGVEVHNAKT KPREEQYNSTYRVVSVLTVLHQDWLNGKEYKC KVSNKALPAPIEKTISKAKGQPREPQVYTLPP SRDELTKNQVSLTCLVKGFYPSDIAVEWESNG QPENNYKTTPPVLDSDGSFFLYSKLTVDKSRW QQGNVFSCSVMHEALHNHYTQKSLSLSPGK |
| 2 | Fc region of human IgG2 without an N-terminal upper hinge region | CPPCPAPPVAGPSVFLFPPKPKDTLMISRTPE VTCVVVDVSHEDPEVQFNWYVDGVEVHNAKTK PREEQFNSTFRVVSVLTVVHQDWLNGKEYKCK VSNKGLPAPIEKTISKTKGQPREPQVYTLPPS REEMTKNQVSLTCLVKGFYPSDIAVEWESNGQ PENNYKTTPPMLDSDGSFFLYSKLTVDKSRWQ QGNVFSCSVMHEALHNHYTQKSLSLSPGK |
| 3 | Human IgG3 Fc region without N-terminal upper hinge region | CPRCPAPELLGGPSVFLFPPKPKDTLMISRTP EVTCVVVDVSHEDPEVQFKWYVDGVEVHNAKT KPREEQYNSTFRVVSVLTVLHQDWLNGKEYKC KVSNKALPAPIEKTISKTKGQPREPQVYTLPP SREEMTKNQVSLTCLVKGFYPSDIAVEWESSG QPENNYNTTPPMLDSDGSFFLYSKLTVDKSRW QQGNIFSCSVMHEALHNRFTQKSLSLSPGK |
| 4 | Human IgG4 Fc region without N-terminal upper hinge region | CPSCPAPEFLGGPSVFLFPPKPKDTLMISRTP EVTCVVVDVSQEDPEVQFNWYVDGVEVHNAKT KPREEQFNSTYRVVSVLTVLHQDWLNGKEYKC KVSNKGLPSSIEKTISKAKGQPREPQVYTLPP SQEEMTKNQVSL TCLVKGFYPSDIAVEWESNGQPENNYKTTPPV LDSDGSFFLYSRLTVDKSRWQEGNVFSCSVMH NEALHHYTQKSLSLSLGK |
| 5 | Fc region of human IgG1 G1m3 without N-terminal upper hinge region | CPPCPAPELLGGPSVFLFPPKPKDTLMISRTP EVTCVVVDVSHEDPEVKFNWYVDGVEVHNAKT KPREEQYNSTYRVVSVLTVLHQDWLNGKEYKC KVSNKALPAPIEKTISKAKGQPREPQVYTLPP SREEMTKNQVSLTCLVKGFYPSDIAVEWESNG QPENNYKTTPPVLDSDGSFFLYSKLTVDKSRW QQGNVFSCSVMHEALHNHYTQKSLSLSPGK |
| 6 | Fc region of human IgG1 G1m1.17 with N-terminal upper hinge region (residues 216-447 according to the EU index or equivalent in Kabat) | EPKSCDKTHTCPPCPAPELLGGPSVFLFPPKP KDTLMISRTPEVTCVVVDVSHEDPEVKFNWYV DGVEVHNAKTKPREEQYNSTYRVVSVLTVLHQ DWLNGKEYKCKVSNKALPAPIEKTISKAKGQP REPQVYTLPPSR DELTKNQVSLTCLVKGFYPSDIAVEWESNGQP ENNYKTTPPVLDSDGSFFLYSKLTVDKSRWQQ GNVFSCSVMHEALHNHYTQKSLSLSPGK |

-continued

| SEQ ID NO: | Protein | Sequence |
|---|---|---|
| 7 | Fc Region of Human IgG2 with N-terminal upper hinge region | ERKCCVECPPCPAPPVAGPSVFLFPPKPKDTL MISRTPEVTCVVVDVSHEDPEVQFNWYVDGVE VHNAKTKPREEQFNSTFRVVSVLTVVHQDWLN GKEYKCKVSNKGLPAPIEKTISKTKGQPREPQ VYTLPPSREEMTKNQVSLTCLVKGFYPSDIAV EWESNGQPENNYKTTPPMLDSDGSFFLYSKLT VDKSRWQQGNVFSCSVMHEALHNHYTQKSLSL SPGK |
| 8 | Human IgG3 Fc region with N-terminal upper hinge region | ELKTPLGDTTHTCPRCPEPKSCDTPPPCPRCP EPKSCDTPPPCPRCPEPKSCDTPPPCPRCPAP ELLGGPSVFLFPPKPKDTLMISRTPEVTCVVV DVSHEDPEVQFKWYVDGVEVHNAKTKPREEQY NSTFRVVSVLTV LHQDWLNGKEYKCKVSNKALPAPIEKTISKTK GQPREPQVYTLPPSREEMTKNQVSLTCLKGF YPSDIAVEWESSGQPENNYNTTPPMLDSDGSF FLYSKLTVDKSRWQQGNIFSCSVMHEALHNRF TQKSLSLSPGK |
| 9 | Human IgG4 Fc region with N-terminal upper hinge region G1m3 human IgG1 | ESKYGPPCPSCPAPEFLGGPSVFLFPPKPKDT LMISRTPEVTCVVVDVSQEDPEVQFNWYVDGV EVHNAKTKPREEQFNSTYRVVSVLTVLHQDWL NGKEYKCKVSNKGLPSSIEKTISKAKGQPREP QVYTLPPSQEEM TKNQVSLTCLVKGFYPSDIAVEWESNGQPENN YKTTPPVLDSDGSFFLYSRLTVDKSRWQEGNV FSCSVMHEALHNHYTQKSLSLSLGK |
| 10 | Fc region with N-terminal upper hinge region | EPKSCDKTHTCPPCPAPELLGGPSVFLFPPKP KDTLMISRTPEVTCVVVDVSHEDPEVKFNWYV DGVEVHNAKTKPREEQYNSTYRVVSVLTVLHQ DWLNGKEYKCKVSNKALPAPIEKTISKAKGQP REPQVYTLPPSR EEMTKNQVSLTCLVKGFYPSDIAVEWESNGQP ENNYKTTPPVLDSDGSFFLYSKLTVDKSRWQQ GNVFSCSVMHEALHNHYTQKSLSLSPGK |

EXAMPLES

The following examples are given to illustrate various embodiments of the invention.

Example 1 Production of Fc Variants According to the Invention by Directed Mutagenesis 1. Construction of Fc Variants:

Each mutation of interest in the Fc fragment was inserted independently into an expression vector containing the anti-CD20 heavy chain by overlap PCR using two sets of primers adapted to integrate a deletion or a degenerate codon (NNN or NNK) in a targeted position (240 to 243, 258 to 267, 290 to 296, 298 to 305). The fragments thus obtained by PCR were combined and the resulting fragment was amplified by PCR using standard protocols. The PCR product was purified on 1% (w/v) agarose gels, digested with the appropriate restriction enzymes and cloned into the eukaryotic expression vector pMGM05-CD20 (pCEP4 InvitroGen), which contains cloning sites for the Fc fragment (BamHI and NotI) and the VH variable chain of the anti-CD20 antibody. This construction leads to the mutation of two amino acids in Fc (aa224 and 225, HT changed to GS) and the addition of the EFAAA sequence to the C-terminal of Fc, but makes it possible to very rapidly test a very large number of clones.

Initially, it was verified that these mutations did not modify the binding of IgG-WT to the different receptors.

The DNA of isolated clones was sequenced on colonies after PCR. After bioinformatic analyzes, clones with new mutations were frozen at −80° C. with XL1-Blue bacteria and the sequences included in our database.

2. Production of Variant IgG in HEK293 Cells:

The light chain of the anti-CD20 was inserted in a pCEP4 vector identical to the vector used for the heavy chain, denoted pMGM01-CDC20 (pCEP4 InvitroGen). HEK293-F Freestyle™ cells (Invitrogen), grown in 24-well plates, were co-transfected with pMGM01-CD20 and pMGM05-CD20 vectors (Fc-WT and variants) in equimolar amounts (250 ng/ml). with a transfection reagent (1 µl/ml) using standard protocols (Invitrogen). The cells were cultured in suspension in serum-free medium for 7-9 days post-transfection and the IgG-containing supernatants (1 ml) were harvested after centrifugation of the cells at 100 g for 10 min. IgG secreted in the supernatants were quantified using an ELISA test (FastELISA, R&D biotech).

TABLE 1 list of mutants generated

| Name of the mutant | mutations |
|---|---|
| ZAC1-36 | V240H |
| ZAC1-136 | V240I |
| ZAC1-123 | V240M |
| ZAC1-78 | V240N |
| ZAC1-226 | V240S |
| ZAC1-100 | F241H |
| ZAC1-220 | F241Y |
| ZAC1-134 | L242A |
| ZAC1-121 | L242F |
| ZAC1-110 | L242G |
| ZAC1-150 | L242H |
| ZAC1-09 | L242I |
| ZAC1-66 | L242K |
| ZAC1-17 | L242P |
| ZAC1-224 | L242S |
| ZAC1-229 | L242T |
| ZAC1-177 | L242V |
| ZAC1-08 | F243L |
| ZAC1-115 | F243S |
| ZAC2-158 | E258G |
| ZAC2-167 | E258I |
| ZAC2-210 | E258R |
| ZAC2-30 | E258M |
| ZAC2-111 | E258Q |
| ZAC2-86 | E258Y |
| ZAC2-150 | V259C |
| ZAC2-74 | V259I |
| ZAC2-180 | V259L |
| ZAC2-36 | T260H |
| ZAC2-114 | T260I |
| ZAC2-250 | T260M |
| ZAC2-162 | T260N |
| ZAC2-124 | T260R |
| ZAC2-110 | T260S |
| ZAC2-258 | T260W |
| ZAC2-85 | T260A |
| ZAC2-226 | V262A |
| ZAC2-153 | V262S |
| ZAC2-39 | V263T |
| ZAC2-107 | V264L |
| ZAC2-42 | V264S |
| ZAC2-156 | V264T |
| ZAC2-148 | V266L |
| ZAC2-122 | V266M |
| ZAC2-225 | S267A |
| ZAC2-64 | S267Q |
| ZAC2-121 | S267V |
| ZAC3-182 | K290D |
| ZAC3-174 | K290E |

TABLE 1-continued list of mutants generated

| Name of the mutant | mutations |
|---|---|
| ZAC3-83 | K290G |
| ZAC3-70 | K290H |
| ZAC3-62 | K290L |
| ZAC3-246 | K290N |
| ZAC3-54 | K290Q |
| ZAC3-41 | K290R |
| ZAC3-203 | K290S |
| ZAC3-172 | K290Y |
| ZAC3-39 | P291G |
| ZAC3-08 | P291Q |
| ZAC3-185 | P291R |
| ZAC3-13 | R292I |
| ZAC3-71 | R292L |
| ZAC3-196 | E293A |
| ZAC3-178 | E293D |
| ZAC3-61 | E293G |
| ZAC3-126 | E293M |
| ZAC3-120 | E293Q |
| ZAC3-10 | E293S |
| ZAC3-15 | E293T |
| ZAC3-118 | E294A |
| ZAC3-53 | E294G |
| ZAC3-82 | E294P |
| ZAC3-80 | E294Q |
| ZAC3-02 | E294R |
| ZAC3-105 | E294T |
| ZAC3-66 | E294V |
| ZAC3-48 | Q295I |
| ZAC3-254 | Q295M |
| ZAC3-110 | Y296H |
| ZAC3-42 | Y296W |
| ZAC4-192 | S298A |
| ZAC4-130 | S298R |
| ZAC4-233 | Y300I |
| ZAC4-14 | Y300V |
| ZAC4-71 | Y300W |
| ZAC4-187 | R301A |
| ZAC4-218 | R301M |
| ZAC4-255 | R301P |
| ZAC4-03 | R301S |
| ZAC4-268 | V302A |
| ZAC4-131 | V302F |
| ZAC4-237 | V302L |
| ZAC4-53 | V302M |
| ZAC4-236 | V302R |
| ZAC4-29 | V302S |
| ZAC4-208 | V303S |
| ZAC4-144 | V303Y |
| ZAC4-219 | S304T |
| ZAC4-33 | V305A |
| ZAC4-229 | V305F |
| ZAC4-262 | V305I |
| ZAC4-139 | V305L |
| ZAC4-36 | V305R |
| ZAC4-179 | V305S |

Example 2: Fc Receptor Binding Tests

1. Recombinant Fc Receptors Used:

CD16a is an activating receptor that has a V/F polymorphism at position 158 at the Fc binding site. The affinity is better for CD16aV. CD16aV is commercially available (R&D system).

CD32a is an activating receptor that has an H/R polymorphism at position 131 at the Fc binding site. Affinity is better for CD32aH. CD32aH was produced by PX'Therapeutics. CD32aR and CD32b are commercially available (R&D system).

2. ELISA Assays of IgG Variants Produced in the Supernatants of HEK293-F Cells:

IgG variants were tested for binding to several human FcR and FcR by ELISA. Maxisorp immunoplates were coated with 0.1 µg CD32aH/well, or 0.2 µg CD16a/well in PBS or 0.25 µg FcRn in P6 (100 mM sodium phosphate, 50 mM sodium chloride pH6.0). NiNTA plates (HisGrab Pierce) were coated with 0.05 µg CD32aR/well, or 0.2 µg CD32b/well in PBS. After coating overnight at 4° C., the plates were washed twice with PBS (or P6)/0.05% Tween-20 and saturated with PBS/4% BSA (or P6 4% skim-milk) for 2 hours at 37° C. In parallel, the supernatants were diluted in PBS (or P6 for the FcRn test) to a final concentration of 0.5 µg of IgG/ml and mixed with F(ab')2 of IgG HRP from goat anti-human at the same concentration for 2 hours at room temperature. IgG aggregated with F(ab')2 are then incubated with gentle shaking for 1 hour at 30° C. on saturated ELISA plates without dilution for CD16aV, CD32aR and CD32b (i.e. IgG at 0.5 µg/ml), diluted in PBS at 0.25 µg/ml for CD32aH and diluted in P6 at 0.035 µg/ml for FcRn. The plates are then revealed with TMB (Pierce) and the absorbance is read at 450 nm.

Using this ELISA test, the constructed variants were tested in comparison with the wild-type Fc (Fc-WT) and their variant/Fc-WT ratio was calculated, as indicated in Table 2 below. The ELISA tests performed on these variants show a ratio greater than 2 for at least one of the FcγRs tested.

TABLE 2

ELISA CD16aV, CD32aH, CD32aR and CD32b receptor binding assays. The results are expressed in an Fc ratio variant according to the invention/Fc-WT

| Variant name | Mutations | CD16aV | CD32aH | CD32aR | CD32b |
|---|---|---|---|---|---|
| ZAC1-36 | V240H | 1.91 | 2.00 | 0.82 | 0.78 |
| ZAC1-136 | V240I | 3.91 | 3.59 | 1.71 | 1.45 |
| ZAC1-123 | V240M | 4.10 | 2.16 | 1.08 | 1.03 |
| ZAC1-78 | V240N | 2.44 | 1.42 | 0.64 | 0.89 |
| ZAC1-226 | V240S | 3.82 | 2.51 | 0.82 | 0.81 |
| ZAC1-100 | F241H | 0.77 | 3.47 | 1.44 | 1.44 |
| ZAC1-220 | F241Y | 1.60 | 5.50 | 1.84 | 1.10 |
| ZAC1-134 | L242A | 3.75 | 3.06 | 1.75 | 1.41 |
| ZAC1-121 | L242F | 5.89 | 5.31 | 1.47 | 1.38 |
| ZAC1-110 | L242G | 4.40 | 2.71 | 1.43 | 1.35 |
| ZAC1-150 | L242H | 1.19 | 2.04 | 1.14 | 1.36 |
| ZAC1-09 | L242I | 5.11 | 4.99 | 1.77 | 1.58 |
| ZAC1-66 | L242K | 7.27 | 2.87 | 3.04 | 1.32 |
| ZAC1-17 | L242P | 1.47 | 2.50 | 1.19 | 1.14 |
| ZAC1-224 | L242S | 3.34 | 2.00 | 0.88 | 0.91 |
| ZAC1-229 | L242T | 1.49 | 2.11 | 1.65 | 1.40 |
| ZAC1-177 | L242V | 2.49 | 6.68 | 1.96 | 1.70 |
| ZAC1-08 | F243L | 5.15 | 2.23 | 1.60 | 1.46 |
| ZAC1-115 | F243S | 2.25 | 1.48 | 1.50 | 1.38 |
| ZAC2-158 | E258G | 1.16 | 6.81 | 1.45 | 1.29 |
| ZAC2-167 | E258I | 2.03 | 6.78 | 1.83 | 1.29 |
| ZAC2-30 | E258M | 1.28 | 4.52 | 1.56 | 1.52 |
| ZAC2-111 | E258Q | 1.88 | 8.75 | 1.55 | 0.85 |
| ZAC2-210 | E258R | 1.66 | 8.17 | 3.70 | 2.60 |
| ZAC2-86 | E258Y | 1.53 | 5.86 | 2.30 | 2.70 |
| ZAC2-150 | V259C | 1.23 | 2.91 | 2.03 | 1.44 |
| ZAC2-74 | V259I | 1.06 | 2.20 | 1.47 | 1.10 |
| ZAC2-180 | V259L | 1.19 | 3.08 | 2.14 | 1.84 |
| ZAC2-85 | T260A | 4.68 | 3.89 | 1.65 | 1.55 |
| ZAC2-36 | T260H | 1.16 | 2.43 | 1.19 | 0.91 |
| ZAC2-114 | T260I | 1.91 | 7.06 | 1.46 | 1.00 |
| ZAC2-250 | T260M | 1.06 | 3.80 | 1.29 | 1.71 |
| ZAC2-162 | T260N | 0.94 | 2.99 | 1.57 | 1.27 |
| ZAC2-124 | T260R | 1.09 | 3.45 | 2.60 | 1.42 |
| ZAC2-110 | T260S | 1.44 | 3.71 | 1.74 | 0.91 |
| ZAC2-258 | T260W | 1.49 | 3.54 | 1.40 | 1.24 |

TABLE 2-continued

ELISA CD16aV, CD32aH, CD32aR and CD32b receptor binding assays. The results are expressed in an Fc ratio variant according to the invention/Fc-WT

| Variant name | Mutations | ELISA test results | | | |
|---|---|---|---|---|---|
| | | CD16aV | CD32aH | CD32aR | CD32b |
| ZAC2-226 | V262A | 0.91 | 5.84 | 3.78 | 2.42 |
| ZAC2-153 | V262S | 1,01 | 3.64 | 1.14 | 1.03 |
| ZAC2-39 | V263T | 1.13 | 4.80 | 1.27 | 1.01 |
| ZAC2-107 | V264L | 0.82 | 2.67 | 2.13 | 1.34 |
| ZAC2-42 | V264S | 0.67 | 1.40 | 2.30 | 2.07 |
| ZAC2-156 | V264T | 0.91 | 6.24 | 1.86 | 1.42 |
| ZAC2-148 | V266L | 1.12 | 2.10 | 4.67 | 3.68 |
| ZAC2-122 | V266M | 0.47 | 0.34 | 2.44 | 2.32 |
| ZAC2-225 | S267A | 1.26 | 4.26 | 5.82 | 4.75 |
| ZAC2-64 | S267Q | 0.63 | 0.43 | 2.49 | 3.00 |
| ZAC2-121 | S267V | 0.59 | 0.29 | 2.36 | 2.02 |
| ZAC3-172 | K290Y | 4.79 | 6.72 | 2.16 | 1.00 |
| ZAC3-203 | K290S | 2.28 | 4.70 | 1.76 | 1.21 |
| ZAC3-41 | K290R | 1.12 | 1.58 | 2.15 | 2.39 |
| ZAC3-54 | K290Q | 2.47 | 3.85 | 1.52 | 1.50 |
| ZAC3-246 | K290N | 1.36 | 3.22 | 1.71 | NA |
| ZAC3-62 | K290L | 1.51 | 2.65 | 1.35 | 0.63 |
| ZAC3-70 | K290H | 3.49 | 6.48 | 2.64 | 1.66 |
| ZAC3-83 | K290G | 4.20 | 5.78 | 1.86 | 1.83 |
| ZAC3-174 | K290E | 2.83 | 4.89 | 1.66 | 1.83 |
| ZAC3-182 | K290D | 2.04 | 3.38 | 2.23 | NA |
| ZAC3-185 | P291R | 0.64 | 2.57 | 1.93 | NA |
| ZAC3-08 | P291Q | 1.61 | 2.32 | 0.99 | 0.96 |
| ZAC3-39 | P291G | 1.32 | 2.39 | 1.28 | 1.65 |
| ZAC3-71 | R292L | 1.67 | 2.22 | 0.71 | 0.41 |
| ZAC3-13 | R292I | 0.81 | 2.19 | 0.48 | 0.53 |
| ZAC3-15 | E293T | 0.41 | 1.40 | 2.07 | 1.81 |
| ZAC3-10 | E293S | 1.02 | 2.95 | 1.18 | 1.51 |
| ZAC3-120 | E293Q | 1.78 | 2.17 | 1.49 | NA |
| ZAC3-126 | E293M | 1.32 | 2.42 | 1.81 | NA |
| ZAC3-61 | E293G | 0.48 | 1.37 | 2.44 | 0.89 |
| ZAC3-178 | E293D | 0.79 | 2.68 | 1.80 | NA |
| ZAC3-196 | E293A | 0.89 | 2.99 | 1.91 | NA |
| ZAC3-66 | E294V | 1.00 | 1.91 | 3.03 | 0.93 |
| ZAC3-105 | E294T | 0.80 | 2.34 | 1.13 | NA |
| ZAC3-02 | E294R | 0.71 | 0.90 | 2.09 | 1.58 |
| ZAC3-80 | E294Q | 0.88 | 1.26 | 2.78 | 1.01 |
| ZAC3-82 | E294P | 0.87 | 1.32 | 2.43 | 0.70 |
| ZAC3-53 | E294G | 0.57 | 3.30 | 2.34 | 0.52 |
| ZAC3-118 | E294A | 1.86 | 5.10 | 1.57 | 1.25 |
| ZAC3-254 | Q295M | 1.74 | 2.81 | 1.10 | NA |
| ZAC3-48 | Q295I | 0.92 | 5.36 | 1.29 | 0.58 |
| ZAC3-42 | Y296W | 3.83 | 1.49 | 1.20 | 1.60 |
| ZAC3-110 | Y296H | 2.17 | 0.86 | 0.98 | NA |
| ZAC4-192 | S298A | 5.53 | 0.24 | 0.48 | 0.51 |
| ZAC4-130 | S298R | 4.37 | 0.66 | 1.09 | 0.66 |
| ZAC4-233 | Y300I | 0.69 | 2.25 | 1.01 | 1.04 |
| ZAC4-14 | Y300V | 0.76 | 2.37 | 0.78 | 2.05 |
| ZAC4-71 | Y300W | 0.87 | 2.34 | 1.14 | 1.06 |
| ZAC4-187 | R301A | 0.81 | 1.25 | 2.06 | 2.11 |
| ZAC4-218 | R301M | 0.95 | 1.22 | 1.78 | 2.07 |
| ZAC4-255 | R301P | 0.63 | 4.64 | 0.06 | 0.24 |
| ZAC4-03 | R301S | 1.29 | 2.42 | 1.16 | 1.06 |
| ZAC4-268 | V302A | 1.00 | 2.38 | 1.86 | 3.09 |
| ZAC4-131 | V302F | 0.76 | 2.82 | 1.06 | 0.71 |
| ZAC4-237 | V302L | 0.46 | 0.31 | 3.15 | 4.69 |
| ZAC4-53 | V302M | 0.63 | 1.50 | 2.25 | 1.56 |
| ZAC4-236 | V302R | 0.45 | 0.38 | 5.08 | 10.56 |
| ZAC4-29 | V302S | 1.10 | 2.51 | 1.87 | 1.71 |
| ZAC4-208 | V303S | 0.96 | 1.39 | 1.64 | 2.27 |
| ZAC4-144 | V303Y | 1.00 | 3.50 | 2.10 | 1.03 |
| ZAC4-219 | S304T | 0.98 | 1.82 | 2.14 | 2.34 |
| ZAC4-33 | V305A | 0.55 | 1.00 | 2.20 | 2.04 |
| ZAC4-229 | V305F | 1.34 | 1.11 | 2.15 | 2.40 |
| ZAC4-262 | V305I | 1.22 | 1.26 | 1.87 | 2.22 |
| ZAC4-139 | V305L | 1.19 | 2.72 | 1.87 | 0.82 |
| ZAC4-36 | V305R | 1.33 | 3.50 | 1.71 | 2.42 |
| ZAC4-179 | V305S | 1.29 | 1.65 | 2.03 | 1.66 |

Example 3: Binding Tests for Purified IgG Variants on Fc Receptors

1. ELISA Binding Tests of Purified IgG Variants:

The variants produced in the HEK293-F cell supernatants as described in Example 1, were purified by a conventional protein A affinity chromatography method.

The constructed and purified variants were tested in comparison with wild-type Fc (Fc-WT), according to the protocols below. Their variant/Fc-WT ratio was calculated as shown in Table 3 below.

Human FcRn Binding (hFcRn):

Maxisorp immunoplates were coated with FcRn in pH6 phosphate buffer (250 ng per well) overnight at 4° C. (100 μl/well). After saturation of the plates for 2 hours in pH6 phosphate buffer and 5% skimmed milk, the variant IgG solutions were added to each well at increasing concentrations (from 0.00488 to 10 μg/ml) for 1 h at 37° C., then were contacted with IgG HRP goat anti-Fab human F(ab')2 for 1 h at 37° C. The bound IgGs were detected after revelation at TMB by absorbance measurement at 450 nm.

Human CD64 Binding (hCD64):

Maxisorp immunoplates were coated with the human CD64 receptor (100 ng/well) overnight at 4° C. (100 μl/well). After saturation of the plates for 2 hours in PBS buffer and 4% BSA, the variant IgG solutions were added to each well at increasing concentrations (0.03125 to 1 μg/ml) for 1 h at 37° C. and then placed in contact with goat anti-CK human F(ab')2 of IgG HRP for 1 h at 37° C. The bound IgG were detected after revelation at TMB by absorbance measurement at 450 nm.

Linkage to Human FcγRs:

Maxisorp immunoplates were coated with 50 ng hCD32aH/well, 200 ng hCD16aF/well or 75 ng hCD16aV/well in PBS. Immobilizing nickel chelating plates (Hisgrab Pierce) were coated with 50 ng hCD32aR/well or 100 ng hCD32b/well in PBS. After coating overnight at 4° C., the plates were washed twice with PBS/0.05% Tween-20 and saturated with PBS/4% BSA for 2 hours at 37° C. In parallel, the variant IgG solutions were diluted in PBS to a final concentration of 1 μg of IgG/ml and mixed with F(ab')2 of IgG HRP of goat anti-Fab at the same concentration for 2 hours at room temperature. The F(ab')2 aggregated IgG were then incubated with gentle shaking for 1 hour at 30° C. on saturated ELISA plates at different dilutions in PBS. Plates were then revealed with TMB and the absorbance read at 450 nm.

TABLE 3 hCD16aV, hCD16aF, hCD32aH, hCD32aR, hCD32b, hCD64 and hFcRn ELISA
receptor binding tests with purified variants. The results are
expressed in Fc ratio variant according to the invention/Fc-WT

| Variant name | Mutations | hCD16aV Ratio at 0.25 µg/ml AVERAGE | hCD16aF Ratio at 0.25 µg/ml AVERAGE | hCD64 Ratio at 0.5 µg/ml AVERAGE |
|---|---|---|---|---|
| A3A-184A | K334N/P352S/A378V/V397M | 3.53 ± 0.15 | 2.19 ± 0.36 | 2.11 ± 0.26 |
| A3A-184E | Y296W/K334N/P352S/A378V/V397M | 4.58 ± 0.83 | 4.27 ± 0.13 | 1.54 ± 0.18 |
| ZAC3-42 | Y296W | 2.36 ± 0.07 | 1.63 ± 0.11 | 0.91 ± 0.13 |
| ZAC3-83 | K290G | 1.91 ± 0.10 | 1.43 ± 0.22 | 1.18 ± 0.33 |
| ZAC2-210 | E258R | 1.44 ± 0.97 | 1.26 ± 0.38 | 0.97 ± 0.14 |
| ZAC2-226 | V262A | 0.53 ± 0.10 | 0.77 ± 0.06 | 0.80 ± 0.05 |

| Variant name | Mutations | hFcRn Ratio at 1.25 µg/ml AVERAGE | hCD32aR Ratio at 0.125 µg/ml AVERAGE | hCD32b Ratio at 0.125 µg/ml AVERAGE | hCD32aH Ratio at 0.25 µg/ml AVERAGE |
|---|---|---|---|---|---|
| A3A-184A | K334N/P352S/A378V/V397M | 11.31 ± 1.48 | 1.42 ± 0.14 | 1.96 ± 0.20 | 1.73 ± 0.09 |
| A3A-184E | Y296W/K334N/P352S/A378V/V397M | 9.45 ± 1.02 | 1.33 ± 0.04 | 1.79 ± 0.47 | 1.73 ± 0.07 |
| ZAC3-42 | Y296W | 0.90 ± 0.14 | 1.01 ± 0.04 | 1.14 ± 0.25 | 1.01 ± 0.19 |
| ZAC3-83 | K290G | 0.93 ± 0.14 | 1.17 ± 0.06 | 1.31 ± 0.11 | 1.23 ± 0.03 |
| ZAC2-210 | E258R | 0.79 ± 0.45 | 0.53 ± ND | 0.68 ± ND | 1.22 ± 0.45 |
| ZAC2-226 | V262A | 0.60 ± 0.32 | 0.48 ± ND | 0.63 ± ND | 0.73 ± 0.00 |

2. Octet® Binding Assays (BLI "Bio-Layer Interferometry" Technology, Pall):

Anti Penta-HIS Biosensors (HIS 1K) are used. The hCD16aV receptor (R&D Systems) diluted to 1 µg/ml is immobilized in Kinetics Buffer, i.e. 44 nM. The variant IgG were tested at 1000, 500, 250, 125, 62.5, 31.25, 15 and 0 nM in Kinetics Buffer. KD analysis was performed using a 1:1 association model.

The results are shown in Table 4.

TABLE 4

Octet ® binding assays with purified variants

| Variant name | Mutations | KD hCD16aV [BLI] (nM) | Ratio KD WT/variant |
|---|---|---|---|
| A3A-184A | K334N/P352S/A378V/V397M | 47 | 12.39 |
| A3A-184E | Y296W/K334N/P352S/A378V/V397M | 80 | 7.25 |
| ZAC3-42 | Y296W | 288 | 2.02 |
| ZAC3-83 | K290G | 326 | 1.78 |
| ZAC2-210 | E258R | 411 | 1.41 |
| ZAC1-08 | F243L | 472 | 1.23 |
| ZAC2-85 | T260A | 472 | 1.23 |
| ZAC1-123 | V240M | 491 | 1.18 |
| ZAC1-121 | L242F | 512 | 1.13 |
| ZAC2-226 | V262A | 518 | 1.12 |
| ZAC1-110 | L242G | 541 | 1.07 |
| Fc-WT | SEQ ID NO: 1 | 580 | 1.00 |

Example 3: Production of Additional IgG Variants in HEK293 Cells

Combinations of mutants comprising at least one mutation i) according to the invention were produced from an Fc fragment comprising the N315D/A330V/N361D/A378V/N434Y (T5A-74 mutant) or V259I/N315D/N434Y (C6A_74 mutant) or N315D/N361D/A378V/N434Y (T5A_74A mutant) or K334N/P352S/V397M/A378V (A3A_184A mutant). They are shown in Table 5.

TABLE 5

Additional variants generated in the context of the invention

| Name | Va Starting variant | Mutation i) according to the invention added | List of mutations combined |
|---|---|---|---|
| T5A-74I | T5A-74 | T260A | T260A/N315D/A330V/N361D/A378V/N434Y |
| T5A-74J | T5A-74 | E258I | E258I/N315D/A330V/N361D/A378V/N434Y |
| T5A-74K | T5A-74 | K290Y | K290Y/N315D/A330V/N361D/A378V/N434Y |
| T5A-74L | T5A-74 | E294A | E294A/N315D/A330V/N361D/A378V/N434Y |
| T5A-74M | T5A-74 | Y296W | Y296W/N315D/A330V/N361D/A378V/N434Y |
| C6A_74W | C6A_74 | Y296W | Y296W/V259I/N315D/N434Y |
| C6A_74G | C6A_74 | K290G | K290G/V259I/N315D/N434Y |
| T5A-74MA | T5A_74A | Y296W | Y296W/N315D/N361D/A378V/N434Y |
| T5A_74AG | T5A_74A | K290G | K290G/N315D/N361D/A378V/N434Y |
| A3A_184AY | A3A_184A | N434Y | N434Y/K334N/P352S/V397M/A378V |
| A3A_184E | A3A_184A | Y296W | Y296W/K334N/P352S/V397M/A378V |
| A3A_184AG | A3A_184A | K290G | K290G/K334N/P352S/V397M/A378V |

The invention claimed is:

1. A variant of a parent polypeptide comprising a human IgG1 Fc fragment, wherein the variant has an increased affinity for at least one of the Fc (FcR) fragment receptors selected from among FcγRIIIa (CD16a), FcγRIIa (CD32a) and FcγRIIb (CD32b) receptors, relative to that of the parent polypeptide, wherein the variant comprises at least the mutation Y296W, of the Fc fragment; and
   (i) a mutation chosen from 334N, 378V and 397M; and
   ii) at least three mutations chosen from 334N, 352S, 378V and 397M, with the condition that mutations (i) and (ii) do not occur on the same amino acids, wherein the numbering is that of the EU index or equivalent in Kabat.

2. Variant according to claim 1, having an increased affinity for the FcγRIIIa (CD16a) receptor.

3. Variant according to claim 1, characterized in that it is selected from an isolated Fc fragment, a sequence derived from an isolated Fc fragment, an antibody and a fusion protein comprising an Fc fragment.

4. Variant of a parent polypeptide according to claim 1, characterized in that it is an antibody.

5. Variant according to claim 1, directed against an antigen selected from a tumor antigen, a viral antigen, a bacterial antigen, a fungal antigen, a toxin, a membrane or circulating cytokine and a membrane receptor.

6. Pharmaceutical composition comprising (1) a variant according to claim 1, and (2) at least one pharmaceutically acceptable excipient.

* * * * *